United States Patent
Ren et al.

(10) Patent No.: US 9,616,027 B2
(45) Date of Patent: Apr. 11, 2017

(54) PRAMIPEXOLE SUSTAINED RELEASE TABLET FORMULATION AND MANUFACTURING METHOD THEREOF AND USE THEREOF

(71) Applicant: SHIJIAZHUANG RAPISTEP PHARMACEUTICAL TECHNOLOGY R&D INC., Shijiazhuang, Hebei (CN)

(72) Inventors: Qing Ren, Shijiazhuang (CN); Chaoyun Hu, Shijiazhuang (CN); Jingya Song, Shijiazhuang (CN); Xizheng Ma, Shijiazhuang (CN)

(73) Assignee: SHIJIAZHUANG RAPISTEP PHARMACEUTICAL TECHNOLOGY R&D INC., Hebel (CN)

( * ) Notice: Subject to any disclaimer, the term of this patent is extended or adjusted under 35 U.S.C. 154(b) by 0 days.

(21) Appl. No.: 14/761,176

(22) PCT Filed: Oct. 9, 2014

(86) PCT No.: PCT/CN2014/088205
§ 371 (c)(1),
(2) Date: Jul. 15, 2015

(87) PCT Pub. No.: WO2015/051747
PCT Pub. Date: Apr. 16, 2015

(65) Prior Publication Data
US 2016/0038423 A1    Feb. 11, 2016

(30) Foreign Application Priority Data
Oct. 12, 2013   (CN) .......................... 2013 1 0475466

(51) Int. Cl.
*A61K 31/428* (2006.01)
*A61K 9/20* (2006.01)

(52) U.S. Cl.
CPC .......... *A61K 9/2054* (2013.01); *A61K 9/2013* (2013.01); *A61K 9/2027* (2013.01); *A61K 9/2095* (2013.01); *A61K 31/428* (2013.01)

(58) Field of Classification Search
CPC .. A61K 31/428; A61K 9/2013; A61K 9/2027; A61K 9/2054; A61K 9/2095
See application file for complete search history.

(56) References Cited

U.S. PATENT DOCUMENTS

| 7,695,734 | B2 | 4/2010 | Friedl et al. |
| 2006/0051417 | A1 | 3/2006 | Friedl et al. |
| (Continued) | | | |

FOREIGN PATENT DOCUMENTS

| CN | 101005831 A | 7/2007 |
| CN | 101005830 B | 9/2010 |
| (Continued) | | |

OTHER PUBLICATIONS

Jan. 12, 2015 International Search Report issued in International Patent Application No. PCT/CN2014/088205.

*Primary Examiner* — Ernst V Arnold
(74) *Attorney, Agent, or Firm* — Oliff PLC

(57) ABSTRACT

The present invention relates to a method for preparing the sustained-release tablets via direct compression process, wet granulation process or dry granulation process to obtain the formulations. The present invention also provides a use of the sustained-release tablet formulation of pramipexole in the preparation of pharmaceutical compositions. A sustained release tablet formulation has advantages as follows: breaking out patent monopoly of the innovator preparation, drug dissolution release effects in vitro can be achieved and probably clinical treatment effects can also be accomplished (Continued)

consistent with that of the innovator preparation; abandoning anionic polymers used in the innovator preparation such that making the drug release and absorption not being influenced by the patent body's gastric pH values, in order to avoid the disadvantages of the innovator preparation. Once the tablet formulation is authorized to marketing, the price will be lowered, capable of bringing out effective medical treatment and economical spending for patients.

9 Claims, 3 Drawing Sheets

(56) References Cited

U.S. PATENT DOCUMENTS

2009/0182024 A1  7/2009  Friedl et al.
2013/0274300 A1  10/2013 Friedl et al.

FOREIGN PATENT DOCUMENTS

| | | | | |
|---|---|---|---|---|
| CN | 102406626 A | | 4/2012 | |
| EP | WO 2006015942 | * | 2/2006 | ............... A61K 9/20 |
| WO | 2004/010997 A1 | | 2/2004 | |

* cited by examiner

PRAMIPEXOLE SUSTAINED RELEASE TABLET FORMULATION AND MANUFACTURING METHOD THEREOF AND USE THEREOF

TECHNICAL FIELD

The present invention relates to the field of Pharmaceutical technology, in particular, to a pramipexole sustained release tablet formulation, manufacturing method and use thereof.

BACKGROUND

Pramipexole is a known dopamine D2 receptor agonist. It is structurally different from the ergot-derived drugs, for example, such as bromocriptine or pergolide. It is a full agonist of dopamine, with receptor selectivity for dopamine D2 family.

Pramipexole is designated chemically as (S)-2-Amino-4,5,6,7-tetrahydro-6-(propylamino) benzothiazole, and has molecular formula $C_{10}H_{17}N_3S$ and a relative molecular weight of 211.33. The chemical formula is as follows:

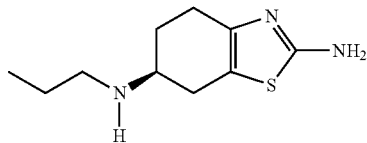

Pramipexole salt generally used is pramipexole dihydrochloride monohydrate (pramipexole dihydrochloride monohydrate) (molecular formula $C_{10}H_{17}N_3S$; relative molecular weight of 302.27). Pramipexole dihydrochloride monohydrate is a white to yellow-white, odorless, crystalline powder. Melting occurs in the range of 296° C. to 301° C., with decomposition. Pramipexole is a chiral compound with a chiral center.

In 1997, pramipexole immediate release (IR) tablet is first approved in the United States. Subsequently, marketing authorized in the European Union, Switzerland, Canada, South America, the countries in Eastern Europe and Asia. Pramipexole dihydrochloride monohydrate is highly soluble compound. Water-solubility of Pramipexole is greater than 20 mg/ml, a solubility in a pH 2 to pH 7.4 buffer media is generally higher than 10 mg/ml. Pramipexole dihydrochloride monohydrate is non-hygroscopic, having high crystalline nature. Crystal modification (monohydrate) of pramipexole does not change under grinding. Pramipexole in the solid state is very stable, and its solution is light sensitive.

A clinical study has shown that pramipexole immediate release tablet formulation combined with levodopa could be used for the treatment of signs and symptoms of Parkinson's disease in the early or advanced stages. IR tablet has to be taken three times a day. The results of three clinical experiments such as a multiple center, randomized double-blind comparison, placebo-controlled experiment have shown that, in the case of administering levodopa to treat early Parkinson's patient, simultaneously administering pramipexole extended release tablet with daily dose increasing from 0.375 mg to 3 mg. At 18 weeks of treatment, UPDRS score is −8.1 for the treatment group, and −5.1 for the placebo group, there is a statistical difference between the two groups. At 33 weeks of treatment, UPDRS score is −8.6 for the treatment group, and UPDRS score is −3.8 for the placebo group, treating effect is not caused by ages or sex according to the course of the study. For patients with advanced Parkinson's disease, there are the fluctuations of movement staying in the "off" state for at least 2 h every day. When administering levodopa with pramipexole simultaneously, a dosage with starting dose of 0.375 mg, gradually increased to 4.5 mg within 7 weeks, and then administering for 26 weeks continuously according to the efficacy and tolerability of the treated subject. The dose of levodopa shall be reduced, in case of adverse reaction of dopaminergic drug occurred. At 18 weeks of treatment, UPDRS score is −11.0 for the treatment group, and UPDRS score is −6.1 for the placebo group. The regulation change of the "off" state for treatment group is −2.1 h, and −1.4 h for that of the placebo group. At 33 weeks of treatment, UPDRS score is −11.1 for the treatment group, and UPDRS score is −6.8 for the placebo group. In view of the pharmacokinetic point, pramipexole IR tablet are able to be completely and rapidly absorbed after oral administration. Its absolute bioavailability is greater than 90%, and the maximum plasma concentration occurs from 1 to 3 hours. Food intake shall influence absorption of pramipexole. Pramipexole displays linear kinetic characteristics, and its changes in plasma level of patients are relatively smaller. The elimination half-life of pramipexole is 8 hours for young people, 12 hours for elder people.

It is well known, the improvement of the active ingredient release allows to simplify the patient's dosing regime by reducing the amount of the daily intake, improving patient's compliance and reducing site effect. Pramipexole extended release tablet formulation is able to meet requirements for the therapeutic effect and capable of reducing the side effect.

A number of prior arts is to provide a composition of the extended release tablet formulation and manufacturing methods thereof.

A sustained-release pharmaceutical composition in form was disclosed in WO 2004/010997, comprising water-soluble salt of pramipexole dispersing in a matrix comprising a hydrophilic polymer and a pregelatinized starch, wherein tensile strength of the said starch is at least 0.15 kN $cm^{-2}$, preferably at least 0.175 kN $cm^{-2}$, more preferably at least 0.2 kN $cm^{-2}$.

According to a preferred embodiment of the invention, there is provided an oral pharmaceutical composition in a tablet form, the tablet containing a core dispersed in the matrix comprising an amount of about 0.375, 0.75, 1.5, 3.5 or 4.5 mg pramipexole dihydrochloride monohydrate, the matrix comprising (a) HPMC type 2208 in an amount of about 35 to 50% of the tablet by weight, and (b) pregelatinized starch with a tensile strength of at least 0.15 kN $cm^{-2}$ in a solid composition of 0.8, in an amount of about 45 to 65% by weight of the tablet, wherein the core is substantially encapsulated in a coating layer in an amount of approximately 2-7% of the tablet by weight, comprising a hydrophobic cellulose and the insoluble component, and pore-forming HPMC component. However, the question raised is that: the artican does not know if the release rate of the composition of a pramipexole extended release tablet according to the above-mentioned invention, is the same or different at different pH values.

Chinese Patent CN101005830 B discloses a composition of pramipexole extended release tablet formulation in an orally dosing form comprising pramipexole or a pharmaceutically acceptable salt thereof dispersed in a matrix, said matrix comprising water swelling polymer of at least two non-pregelatinized starch, one of which is an anionic polymer, preferably is an acrylic polymer, more preferably is a carbomer, in an amount of about 1-10% by weight of the tablet, another one water swelling polymer of the non-pregelatinized starch is a neutral polymer, preferably is hydroxypropyl cellulose, more preferably is hydroxypropyl methylcellulose, in amount of about 25-65% by weight of the tablet. Although the said invention discloses a composition of pramipexole extended release tablet formulation, the active ingredients of the pharmaceutical composition have shown the release characteristics is associated with the pH value, i.e. showing different release rate under the condition of at the same time and at different pH value.

To the inventor's understanding, there is no prior art to disclose a composition of pramipexole extended release tablet formulation to display a pH-independent release profile in the range of pH 1 to pH 7.5, prior to the present invention.

DETAILED DESCRIPTION OF THE PRESENT INVENTION

According to the disadvantages of the prior art, an object of the present invention is to provide a new novel composition of pramipexole extended release tablet formulation or a pharmaceutically acceptable salt thereof, displaying a pH-independent release profile in the range of pH 1.5 to pH 7.5. The present invention also provides a manufacturing method of the tablet composition, comprising a direct compression process, wet granulation process or dry granulation process. Furthermore, the present invention is also to provide the use of an extended release tablet formulation of pramipexole or pharmaceutically acceptable salt thereof, wherein the tablet composition suitable for orally administering once a day, accomplishing the effects of treating Parkinson's disease and the relative complications or symptoms herewith.

The present invention is carried out by the technical solution as follows:

In one aspect of the present invention, the present invention relates to an extended release tablet formulation comprising pramipexole or pharmaceutically acceptable salt thereof, wherein matrix thereof comprising an active ingredient of pramipexole or a pharmaceutically acceptable salt thereof, also comprising at least two water swelling polymers.

In a further aspect of the present invention, the present invention relates to an extended release tablet, wherein the matrix comprising at least two water swelling polymers, wherein at least one of said at least two water swelling polymers is a neutral cellulosic polymer.

The neutral cellulosic polymer may be one or more selected from the group consisting of methylcellulose, hydroxymethylcellulose, ethylcellulose, hydroxyethylcellulose, hydroxypropylcellulose, hydroxybutylcellulose, hydroxyethyl methylcellulose and hydroxypropyl methylcellulose. Suitably, said neutral cellulosic polymer may be one or more selected from the group consisting of methylcellulose, hydroxymethylcellulose, ethylcellulose, hydroxyethylcellulose, hydroxypropylcellulose and hydroxypropyl methylcellulose.

Preferably, the present invention relates to an extended release tablet formulation, wherein the neutral cellulosic polymer may be one or more selected from the group consisting of ethylcellulose, hydroxypropylcellulose and hydroxypropyl methyl cellulose. Most preferably, the neutral cellulosic polymer is hydroxypropyl methylcellulose. More preferably, the present invention relates to an extended release tablet formulation, wherein the content of the cellulosic polymer by weight of the total tablet is from about 5 to about 90%, preferably from about 20 to about 85%, more preferably from about 20 to about 80%, particularly preferred from about 20 to about 50%, or particularly preferred from about 50 to about 80%.

In a furthermore aspect of the present invention, the present invention relates to an extended release tablet formulation, the matrix thereof comprising at least two water swelling polymers, wherein at least one of said at least two water swelling polymers is a neutral noncellulosic polymer.

In a further aspect of the present invention, said noncellulosic polymer may be one or more selected from the group consisting of polyvinylpyrrolidone, polyvinylalcohol, a combination of polyvinylpyrrolidone and vinyl acetate, a combination of polyvinyl-pyrrolidone and polyvinylalcohol, and polyalkylene oxide.

The content of noncellulosic polymer in the matrix is about 4% to about 93% by weight, preferably from about 10% to about 78% by weight, more preferably from about 15% to about 78% by weight, particularly preferably from about 45% to about 78% by weight, or particularly preferably from about 15% to about 48% by weight.

The term "sustained release tablet", "extended release tablet", "composition of a extended release tablet" or "composition of a sustained-release tablet" used herein is refer to a pharmaceutical tablet formulation compressing pramipexole or pharmaceutically acceptable salt thereof, sustained release material and excipients, in some cases, may be interchangeably used one to another having the same meaning.

In a particular aspect of the present invention, the present invention provides a composition of an extended release tablet formulation of pramipexole or a pharmaceutically acceptable salt thereof consisting of pramipexole or a pharmaceutically acceptable salt, at least two water swelling polymer, and excipients, wherein the at least one of said at least two polymers is a neutral cellulosic polymer, and at least the other one of said at least two polymers is a neutral noncellulosic polymer, having the following % by weight of said sustained release tablet formulation:

| | |
|---|---|
| pramipexole or a pharmaceutically acceptable salt thereof | 0.05-4% |
| neutral cellulosic polymer(s) | 5-90% |
| neutral noncellulosic polymer(s) | 4-93% |
| excipients | add to 100% |
| Preferably, pramipexole or a pharmaceutically acceptable salt thereof | 0.05-4% |
| neutral cellulosic polymer(s) | 20-85% |
| neutral noncellulosic polymer(s) | 10-78% |
| excipients | add to 100% |
| More preferably, pramipexole or a pharmaceutically acceptable salt thereof | 0.05-4% |
| neutral cellulosic polymer(s) | 20-80% |
| neutral noncellulosic polymer(s) | 15-78% |
| excipients | add to 100% |
| Particularly preferably, pramipexole or a pharmaceutically acceptable salt thereof | 0.05-4% |
| neutral cellulosic polymer(s) | 20-50% |
| neutral noncellulosic polymer(s) | 45-78% |
| excipients | add to 100% |
| Or particularly preferably, pramipexole or a pharmaceutically acceptable salt thereof | 0.05-4% |
| neutral cellulosic polymer(s) | 50-80% |
| neutral noncellulosic polymer(s) | 15-78% |
| excipients | add to 100% |

As used herein, the term "add to 100% by weight" refers to that if the weight of pramipexole extended release tablet is defined as 100% unit, adding % by weight of pramipexole or a pharmaceutically acceptable salt thereof, a neutral cellulosic polymers and a neutral noncellulosic polymer respectively, finally adding excipients to balance 100% by weight in total mixture, the % by weight of excipients added means "add to 100% by weight"

Particularly preferable extended release tablets consists of pramipexole dihydrochloride monohydrate, hydroxypropyl methylcellulose, the combination of polyvinylpyrrolidone and vinyl acetate, and magnesium stearate.

In a preferred aspect of the present invention is directed to an extended release formulation, matrix thereof comprising pramipexole or a pharmaceutically acceptable salt thereof, further comprising:
  (a) at least one neutral water swelling cellulosic polymer and optionally excipients, the resulting tablet providing a pH-independent in vitro release characteristics in a range of pH 1 to 7.5; and/or
  (b) at least one neutral water swelling noncellulosic polymer and optionally excipients, the resulting tablet providing a pH independent release characteristics in the range of pH 1 to 7.5.

The most preferable matrix of the present invention, comprising (a) at least one neutral water swelling cellulosic polymer and optionally excipients, the resulting tablet providing a pH-independent in vitro release characteristics in a range of pH 1 to 7.5; and/or
  (b) at least one neutral water swelling noncellulosic polymer and optionally excipients, the resulting tablet providing a pH independent release characteristic in the range of pH 1 to 7.5.

The most preferable matrix of the extended release tablet formulation according to the present invention, comprising at least two water swelling polymers, at least one of said at least two polymers is water swelling cellulosic polymer, the other at least one of said at least two polymers is water swelling noncellulosic polymer, and optionally excipients, the obtained tablet has an pH-independent release characteristics.

The extended release tablet formulation in a orally administering form designed according to the present invention requires selection and evaluation of release profile in vitro and at certain times, making it most suitable to obtain the desired plasma characteristics in vivo, preferably the tablet formulation is administered once a day. Therefore, it has been studied on different formulation principles of a single matrix tablet, in order to provide formulations at different release rates. A swellable and partially eroded matrix were used for manufacturing an extended release tablet formulation. As predetermined matrix, the release profile of a sample in vitro can be roughly described based on square root of time release kinetics in order to obtain a pH-independent release profile, i.e. allowing absorption in vivo which is not influenced by pH values in gastrointestinal tract, and helps to avoid self-absorption depending on the pH value of the gastrointestinal tract due to the individual differences. A representative water swelling polymer of the present invention is at least two water swelling polymer constituting the extended release matrix, slowly releasing pramipexole or a pharmaceutically acceptable salt thereof as an active ingredient. After administering, the formulation contact with a liquid containing water, the polymer swells to form a viscous gel layer to adjust the drug release. The viscosity of the polymer is preferably in the range of from 150 mpa·s to 100,000 mpa·s (apparent viscosity of 2% aqueous solution at 20° C.).

As used herein, the term "neutral cellulosic polymers" comprises methylcellulose, ethylcellulose, hydroxymethylcellulose, hydroxyethylcellulose, hydroxypropylcellulose, hydroxybutylcellulose, hydroxyethyl methylcellulose, hydroxypropyl methylcellulose and the like.

As used herein, the term "neutral noncellulosic polymers" comprises polyvinylpyrrolidone, polyvinylalcohol, a combination of polyvinylpyrrolidone and vinyl acetate, a combination of polyvinylpyrrolidone and polyvinylalcohol, and polyalkylene oxide and the like.

Hydroxypropylcellulose and hydroxypropyl methylcellulose at different viscosity grade are commercially available. The viscosity grade of hydroxypropyl methylcellulose applied in the present invention, preferably ranging from about 3,500 mpa·s to about 100,000 mpa·s, particularly preferably ranging from about 5,000 mpa·s to about 100,000 mpa·s, particularly preferably ranging from about 14,000 mpa·s to 100,000 mpa·s (apparent viscosity of 2% aqueous solution at 20° C.). If it is hydroxypropyl methylcellulose K15M and hydroxypropyl methylcellulose K100M, wherein the hydroxypropyl methylcellulose contains 19%-24% methoxy group and 4%-12% hydroxypropyl substituents. Preferably, hydroxypropyl methylcellulose is type 2910 and/or type 2208.

The release of pramipexole or a pharmaceutically acceptable salt thereof from the water swelling polymer matrix exists three main mechanisms: dissolution, erosion and diffusion. When pramipexole or a pharmaceutically acceptable salt thereof homogeneously dispersed in a network structure of soluble matrix polymer, which is released by the dissolution mechanism. The net structure will gradually dissolve in the gastrointestinal tract and gradually release its load drugs thereby. The matrix polymer can also gradually be eroded on the matrix surface, while pramipexole or a pharmaceutically acceptable salt thereof is released at the same time. When the matrix become insoluble polymer, pramipexole is released by diffusion mechanism: gastrointestinal fluids penetrate the insoluble sponge-like matrix, diffuse back the drug loaded.

Therefore, the water swelling polymers constituting the matrix are used to control the pharmacokinetics of the formulation release model. Depending on the amount of water swelling polymer in the formulation, the release model is also changed, for example, a large amount of water swelling polymer may have a more significant effect of extended release and vice versa. In this formulation, a preferred amount of the water swelling polymer ranges from about 5% to 90% by weight.

Furthermore, when the polymer is combined in use, the ratio of the polymers can also influence the release profile of the formulation. A combination with different types of polymer in use can make the different release mechanisms of pramipexole from the matrix. Such the combination may optionally & effectively controls pharmacokinetic release model of the formulation. For example, when using one or more water swelling polymers, in particular, using hydroxypropylcellulose or hydroxypropyl methylcellulose, the weight ratio of hydroxypropyl methylcellulose ranges from about 5 to 80%, the weight ratio of hydroxypropylcellulose ranges from about 0% to about 10%. The release of pramipexole or a pharmaceutically acceptable salt thereof from a matrix containing hydroxypropylcellulose and hydroxypropyl methylcellulose can be completed by a combined set of release mechanisms. Hydroxypropyl methylcellulose will gradually dissolve and erose from the matrix since it has a higher water solubility more than that of hydroxypropylcellulose. hydroxypropylcellulose is a sponge-like matrix, mainly releases the active ingredient by a diffusion release mechanism.

In addition to pramipexole or a pharmaceutically acceptable salt thereof and water swelling polymer, the formulation of the present invention optionally comprises more excipients, i.e. an auxiliary material capable of improving producibility, compressibility, appearance and taste of the formulation. These auxiliary materials include diluents or fillers, glidants, binders, granulating agents, anti-blocking agents, lubricants, flavors, dyes, preservatives, as well as the other known excipients commonly used in the prior art are included.

Lubricants may be used to facilitate the release of the tablet from the mold and prevent it from sticking overshoot. A suitable lubricants comprises magnesium stearate, calcium stearate, hydrogenated vegetable oil, stearic acid, talc powder and the like. Preferably magnesium stearate is used as a lubricant, in an amount of from about 0.1 to about 1.5%, and preferably used in an amount of from about 0.5 to about 1.2%, according to the present invention.

According to the present invention, the extended release tablet matrix consists of pramipexole or a pharmaceutically acceptable salt thereof, a neutral cellulosic polymer (preferably, hydroxypropyl methylcellulose), a neutral noncellulosic polymer (preferably, a combination of polyethylenepyrrolidone and vinyl acetate), and excipients. The amount of hydroxypropyl methylcellulose used ranges from 5 to 90%, preferably from 20 to 85%, more preferably from 20 to 80%, particularly preferably from 20 to 50%, or particularly preferably 50% to 80%. The amount of combination of polyvinylpyrrolidone and vinyl acetate ranges 4-93%, preferably from about 10% to about 78%, more preferably from about 15% to about 78%, particularly preferably 45% to about 78%, or particularly preferably from about 15% to about 48%.

In some particular aspects of the present invention, there is provided a tablet formulation of pramipexole or a pharmaceutically acceptable salt thereof having a pH-independent characteristics and its absorption is not influenced from the tablet by food intake or food after pramipexole or a pharmaceutically acceptable salt thereof is released from the tablet formulation.

In a preferred aspect of the present invention, said extended release tablet matrix contains hydroxypropyl methylcellulose, combination of polyvinylpyrrolidone and vinyl acetate, and magnesium stearate, or substantially consists of hydroxypropyl methylcellulose, combination of polyvinylpyrrolidone and vinyl acetate, and magnesium stearate. The amount of hydroxypropyl methylcellulose ranges preferably from 5 to 90%, more preferably from 20 to 80%, particularly preferably from 25 to 80%. The amount of the combination of polyvinylpyrrolidone and vinyl acetate ranges preferably from 4 to 93%, more preferably from about 10% to about 78%, more preferably from about 15% to about 78%, particularly preferably 45% to about 78%, or particularly preferably from 15% to about 48%. The amount of magnesium stearate preferably ranges from 0.1 to 1.5%, particularly preferably ranges from 0.5 to 1.2%.

The present invention provides an extended release tablet formulation having the following % by weight:

| | |
|---|---|
| pramipexole or a pharmaceutically acceptable salt thereof | 0.05-4% |
| neutral cellulosic polymer(s) | 5-90% |
| neutral noncellulosic polymer(s) | 4-93% |
| excipients | add to 100% |

The present invention provides a particularly preferable extended release tablet formulation having the following % by weight:

| | |
|---|---|
| pramipexole or a pharmaceutically acceptable salt thereof | 0.05-4% |
| neutral cellulosic polymer(s) | 20-50% |
| neutral noncellulosic polymer(s) | 45-78% |
| magnesium stearate | 0.1-1.5% |

Or the present invention provides a particularly preferable extended release tablet formulation having the following % by weight:

| | |
|---|---|
| pramipexole or a pharmaceutically acceptable salt thereof | 0.05-4% |
| neutral cellulosic polymer(s) | 50-80% |
| neutral noncellulosic polymer(s) | 15-78% |
| magnesium stearate | 0.1-1.5% |

In another aspect of the present invention, the present invention relates to a direct compression method to manufacture an extended release tablet formulation comprising the steps of:
(1) pramipexole or a pharmaceutically acceptable salt thereof with the neutral cellulosic polymer(s) to be pre-mixed to obtain a pre-mixture in a mixer;
(2) dry screening the pre-mixture through a screen in order to separate cohesive particles to improve uniformity of the contents;
(3) mixing the pre-mixture of the step (2) in the mixer, and adding the remaining excipients to the mixer and the mixing is to be continued;
(4) the final mixture is tabletted on to a suitable tablet press in order to prepare a matrix tablet. Such that a tablet formulation is prepared according to a direct compression process.

The other methods may also be used for the preparation of pramipexole extended release tablet formulation, such a conventional wet granulation process and dry granulation method. In the case of the wet granulation method, pramipexole with excipients and binders were granulated, excipients and the active ingredient were sufficiently mixed, dried, granulated and tabletted after adding and mixing the lubricant. In the case of dry granulation, the mixture is prepared into a strip form by a conventional roller compactor after mixing pramipexole with excipients, and granulated. The mixture is tabletted after finally adding and mixing with a lubricant.

In another aspect of the present invention, the present invention relates to a wet granulation method to manufacture an extended release tablet formulation comprising the steps of:
(1) pramipexole or a pharmaceutically acceptable salt thereof with the neutral cellulosic polymer(s) to be pre-mixed to obtain a pre-mixture in a mixer;
(2) dry screening the pre-mixture through a screen in order to separate cohesive particles to improve uniformity of the contents;
(3) mixing the pre-mixture of the step (2) in the mixer, and adding the neutral noncellulosic polymer(s) to the mixer and mixing is to be continued;
(4) by adding a suitable binder or wetting agent, the mixture of step (3) is made into wet granules;
(5) drying the granules of step (4) in a fluidized bed dryer or a drying oven;

(6) mixing the dried granules of step (5) with excipients in the mixer, in order to obtain the final mixture;

(7) the final mixture of step (6) is tabletted on to a suitable tablet press in order to prepare a matrix tablet.

In another particular aspect of the present invention, the present invention relates to a dry granulation method to manufacture an extended release tablet formulation comprising the steps of:

(1) pramipexole or a pharmaceutically acceptable salt thereof with the neutral cellulosic polymer(s) to be pre-mixed to obtain a pre-mixture in a mixer;

(2) dry screening the pre-mixture through a screen in order to separate cohesive particles to improve uniformity of the contents;

(3) mixing the pre-mixture of the step (2) in the mixer, and adding the neutral noncellulosic polymer(s) to the mixer and mixing is to be continued;

(4) compacting the mixture of the step (3) on to a suitable roller compactor.

(5) suitably milling or sieving the ribbon of small particles obtained from step (4);

(6) mixing the dried granules of step (5) with excipients in the mixer, in order to obtain the final mixture;

(7) the final mixture of step (6) is tabletted on to a suitable tablet press in order to prepare a matrix tablet.

A sustained release tablet formulation of the present invention has the following advantages: breaking out patent monopoly of the innovator preparation, the effects of the drug dissolution release in vitro can be accomplished consistent with that of the innovator preparation and probably clinical treatment effects can also be accomplished consistent with that of the innovator preparation; abandoning anionic polymers used in the innovator preparation, thus making the drug release and absorption not being influenced by the patient body's gastric pH value, in order to overcome the disadvantages of the innovator preparation. Once the tablet formulation is authorized to marketing, the price will be lowered, will be able to bring out both medical effective treatment and economical treatment for patients.

FIGURE DESCRIPTION

EMBODIMENT

Figure 1:
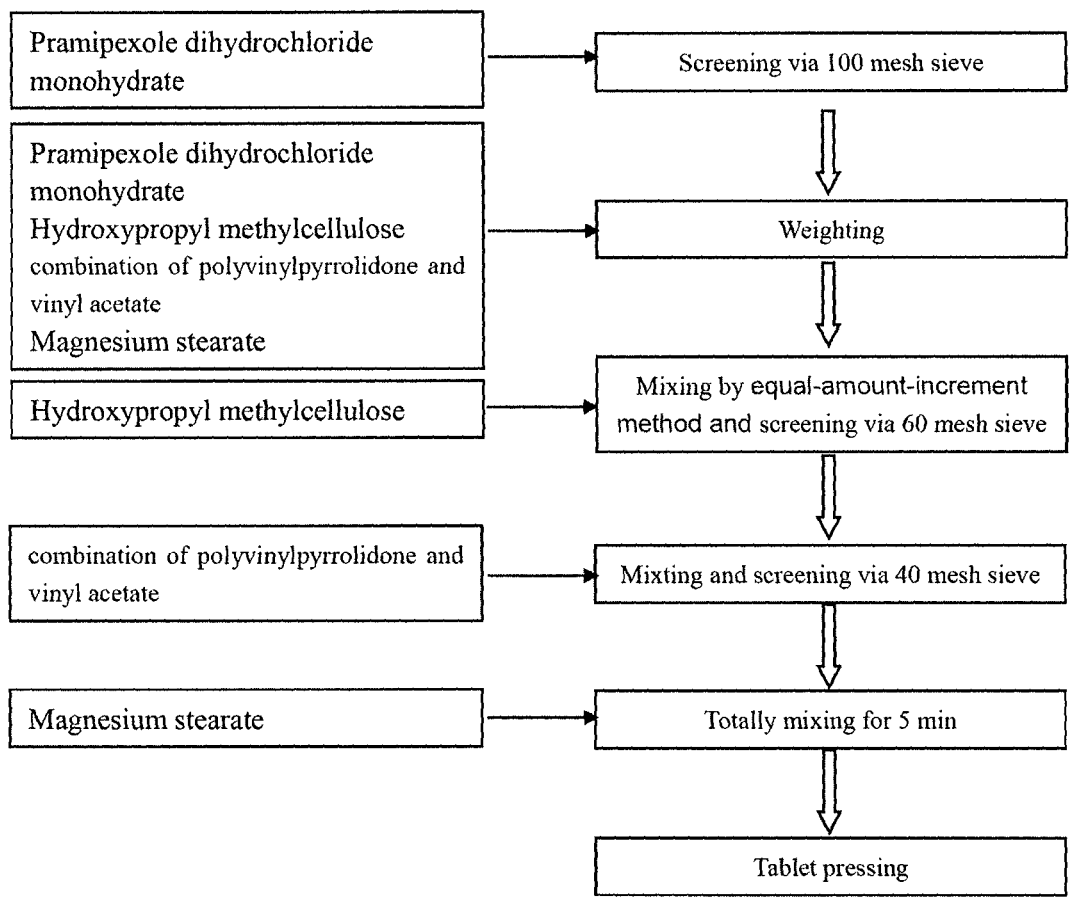
FIG. 1 is a flow chart of a direct compression method applied to prepare a sustained release tablet formulation according to the present invention.
Figure 2:
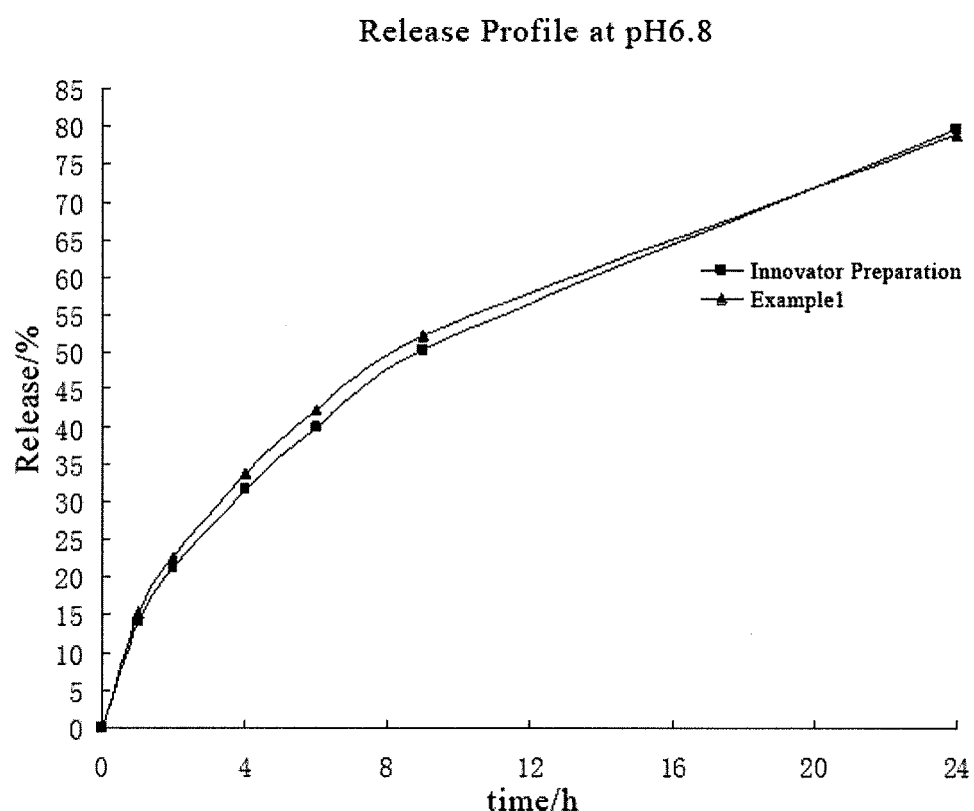
FIG. 2 is a dissolution graph of a sustained release tablet formulation prepared according to present invention comparing with the innovator preparation.

The main indication of pramipexole is for Parkinson's disease, a more common disease usually accompanied by aging and memory loss. Therefore, the extended release matrix tablet or slow release matrix tablet of pramipexole or pramipexole pharmaceutically acceptable salt thereof according to the present invention, reducing the amount of recommended daily intake for patients, simplifying dosing regime and improving patient's compliances, particularly suitable for aging patients. Preferably, the extended release tablet formulation of the present invention is to provide a daily dosing formulation for administering once a day.

The tablet formulation according to the present invention may be manufactured via a direct compression process, a wet granulation process or a dry granulation process.

The term "innovator preparation" used herein refers to a medical pramipexole extended release tablet formulation, i.e. "MIRAPEXER" produced by Boehringer Ingelheim, used as a contrary example herewith in the embodiment according to the present invention.

The term "active ingredient" used herein refers to a pharmaceutical composition capable of having a treating effect on a certain disease or pathological symptom, in particular, used herein refer to pramipexole or a pharmaceutically acceptable salt thereof, having a treating effect on Parkinson's disease and complications or symptoms associated herewith.

The term "sustained release material" or "extended release material" used herein refers to an auxiliary material meaning all the materials functionally influencing drug dissolution and diffusion from the formulation when the pharmaceutical formulation is designed and added hereto, controlling the concentration on absorption site and delaying absorption thereof, in particular, refers to neutral cellulosic polymer and/or neutral noncellulosic polymer according to the present invention.

In another embodiment of the present invention, there is provided the use of a sustained release tablet formulation for manufacturing a pharmaceutical composition in order to treat Parkinson's disease and relative complications or pathological symptoms.

Said use comprises administering a therapeutically effective amount of pramipexole extended release tablets to human. As used herein, the term "therapeutically effective amount" refers to a quantity sufficient to achieve a desired therapeutic and/or prophylactic effect, e.g., an amount which results in the prevention of, or a decrease in, the symptoms associated herewith. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. The skilled artisan will be able to determine appropriate dosages depending on these and other factors. The compositions can also be administered in combination with one or more additional therapeutic compounds. The method of present invention also comprises capable of administering the composition to a subject having one or more sign of disease or pathological symptoms. For example, a "therapeutically effective amount" refers to the minimum extent to alleviate the symptoms of the physiological role of the average. The daily dose was from 0.1 mg/kg to 10 mg/kg body weight, preferably from about 0.01 mg/kg to 6 mg/kg body weight, more preferably more preferably 0.1 mg/kg to about 6 mg/kg, and most preferably 0.3 mg/kg to about 6 mg/kg body weight. Dosing frequency may be once or twice per day, preferably once a day. Accordingly, a subject of the present invention is to provide a composition of pramipexole extended release tablet formulation capable of administering once a day.

The following examples of the embodiment are for the skilled person in the prior art to simply and readily understand the present invention, but the present invention is not limited to the examples and the specification.

The description of the present invention is further detailed via examples as follows. According to the present invention, a pramipexole extended release tablet formulation is manufactured. Said tablet formulation is coloured with white to yellowish-white, round biconvex tablets. The tablet formulation has to be orally administered and shall not be divided into two halves. In the examples, pramipexole extended release tablet formulation contains 1.5 mg Pramipexole dihydrochloride monohydrate, equivalent to 1.05 mg of free pramipexole in an anhydrous base.

EXAMPLE

Example 1

An embodiment of qualitative and quantitative composition of pramipexole extended release tablet formulation according to the present invention is shown in Table 1 to Table 5 below.

TABLE 1 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 1.5 | 0.43 | Active ingredient | EP7.3 |
| Hydroxypropyl methylcellulose | 240 | 68.57 | Sustained release material | Imported registration standard |
| composition of Polyvinylpyrrolidone and vinyl acetate | 105 | 30.00 | Sustained release material | Imported registration standard |
| Magnesium stearate | 3.5 | 1.00 | Lubricant | CP2005 |
| Total | 350 | | | |

TABLE 2 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 1.5 | 0.43 | Active ingredient | EP7.3 |
| Hydroxypropyl methylcellulose | 235 | 67.14 | Sustained release material | Imported registration standard |
| composition of Polyvinylpyrrolidone and vinyl acetate | 110 | 31.43 | Sustained release material | Imported registration standard |
| Magnesium stearate | 3.5 | 1.00 | Lubricant | CP2005 |
| Total | 350 | | | |

TABLE 3 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 1.5 | 0.43 | Active ingredient | EP7.3 |
| Hydroxypropyl methylcellulose | 230 | 65.71 | Sustained release material | Imported registration standard |
| composition of Polyvinylpyrrolidone and vinyl acetate | 115 | 32.86 | Sustained release material | Imported registration standard |
| Magnesium stearate | 3.5 | 1.00 | Lubricant | CP2005 |
| Total | 350 | | | |

TABLE 4 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 1.5 | 0.43 | Active ingredient | EP7.3 |
| Hydroxypropyl methylcellulose | 225 | 64.29 | Sustained release material | Imported registration standard |
| composition of Polyvinylpyrrolidone and vinyl acetate | 120 | 34.29 | Sustained release material | Imported registration standard |
| Magnesium stearate | 3.5 | 1.00 | Lubricant | CP2005 |
| Total | 350 | | | |

TABLE 5 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 1.5 | 0.43 | Active ingredient | EP7.3 |
| Hydroxypropyl methylcellulose | 220 | 62.86 | Sustained release material | Imported registration standard |
| composition of Polyvinylpyrrolidone and vinyl acetate | 125 | 35.71 | Sustained release material | Imported registration standard |
| Magnesium stearate | 13.5 | 1.00 | Lubricant | CP2005 |
| Total | 350 | | | |

TABLE 6 qualitative and quantitative composition of pramipexole sustained release tablet formulation

| Ingredient | mg/ per 1.5 mg tablet | Weight ratio % | Function | Reference to standard |
|---|---|---|---|---|
| Pramipexole dihydrochloride monohydrate | 0.375 | 0.15 | Active ingredient | EP7.3 |
| Hydroxypropyl methylcellulose | 82 | 32.80 | Sustained release material | Imported registration standard |
| composition of Polyvinylpyrrolidone and vinyl acetate | 165 | 66.00 | Sustained release material | Imported registration standard |
| Magnesium stearate | 2.5 | 1.00 | Lubricant | CP2005 |
| Total | 250 | | | |

Example 2

A batch of pramipexole sustained tablet formulation applied in example 1 is shown in Table 7. The number of the final composition is about 2000 tablets/batch, each of the tablets providing pH-independent release characteristics in the range of pH 1 to pH 7.5.

TABLE 7 the composition of 1.5 mg pramipexole ER tablet formulation per batch

| Ingredient | g/one batch |
|---|---|
| Pramipexole dihydrochloride monohydrate | 3 |
| Hydroxypropyl methylcellulose | 460 |
| composition of Polyvinylpyrrolidone and vinyl acetate | 230 |
| Magnesium stearate | 7 |
| Total | 700 |

Example 3

A preferred embodiment of manufacturing method according to present invention is illustrated in FIG. 1, exemplarily illustrating the process of manufacturing an extended release tablet formulation according to the examples.

Following the preparation step 1 of the flow chart, the active ingredient is mixed with water swelling polymers and excipients for a few minutes to obtain a pre-mixture. The active ingredient with hydroxypropyl methylcellulose were premixed for 5 minutes in the mixer.

Following the preparation step 2 of the flow chart, optionally dry screening is made. The pre-mixture may be pre-sieved manually through a screen, for example a 0.8 mm mesh size of screen, in order to separate cohesive particles to improve uniformity of the contents;

Following the preparation step 3 of the flow chart, mixing the pre-mixture with the remaining excipients for several minutes, preferably 5 minutes. At the movement, the excipients may be added. In addition to the flow chart, magnesium stearate is added to the pre-mixture, then mixing for a few minutes, for example 3 minutes, to obtain the final mixture.

Following the preparation step 4 of the flow chart, the mixture is subject to tabletting. The final mixture is tabletted onto a suitable tablet press so as to prepare a matrix tablet. In order to control and ensure the nature of matrix tablet as desired, tablet hardness, tablet friability and tablet weight of the obtained matrix tablet is subject to a intermediate control process.

Next, pramipexole extended release tablet formulation according to the present invention can be filled into a bottle with high density polyethylene (HDPE). The bottle can be sealed and closed with a screw cap, and labeled. Alternatively, the blister pack may also be used, for example, using a double aluminum foil blister packaging.

Example 4

The release rate test of the obtained tablets according to example 1 of present invention, comparing with that of the innovator preparation was at the same pH value. The release test profile were plotted according to the release test data. It can be seen that the obtained tablets according to example 1 of the present invention has the same release profile in coincidence with the innovator preparation.

Figure 3:
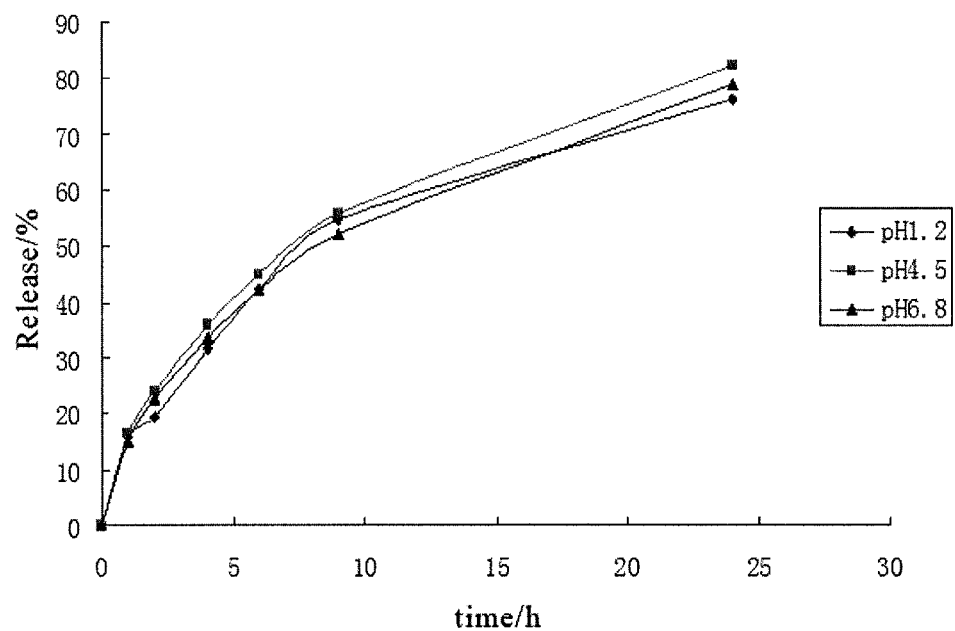
FIG. 3 is a dissolution comparison graph of a sustained release tablets prepared according to example 1 of the present invention at different pH values.

The dissolution rate of the obtained tablets according to example 1 of present invention were determined at different pH values, and dissolution rate were plotted based on the dissolution test data. As shown in FIG. 3, it can be seen that the dissociation rate of the obtained tablets according to example 1 of present invention have consistent release profile in the different pH media, meaning that the release rate is almost not influenced by pH value of the media. However the dissolution rate of the innovator preparation is significantly faster in an acid media, a sustained release effect is not accomplished. Accordingly, the obtained tablets according to example 1 of present invention have advantages more than the innovator preparation.

The invention is not limited to the particular embodiments described herein, which is a single description as a separate aspect of the present invention. A skilled person in the art might understand that the present application may be made in the embodiments, various changes, modifications, substitutions and variations if not departing from the spirit and scope of the application. According to the above descriptions, besides those examples, it is obvious to a skilled person in the art that there are other applications within the same scope or equivalent to those mentioned in the present invention.

The invention claimed is:

1. A pramipexole sustained release tablet formulation, comprises: pramipexole or a pharmaceutically acceptable salt thereof, at least two water swelling polymers and excipients; at least one polymer of said at least two water swelling polymers is a neutral cellulosic polymer, and at least another one polymer of said at least two water swelling polymers is neutral noncellulosic polymer, having the following % by weight of said sustained release tablet formulation:

| | |
|---|---|
| pramipexole or a pharmaceutically acceptable salt thereof | 0.005-4% |
| cellulosic neutral polymer(s) | 62.86-68.57% |
| neutral noncellulosic polymer(s) | 30-35.71% |
| excipients | add to 100%, | wherein said neutral cellulosic polymer(s) is one or more selected from methylcellulose, hydroxymethylcellulose, ethylcellulose, hydroxyethylcellulose, hydroxypropylcellulose and hydroxypropyl methylcellulose, and said neutral noncellulosic polymer(s) is a combination of polyvinylpyrrolidone and vinyl acetate.

2. A pramipexole sustained release tablet formulation according to claim 1, wherein; said neutral cellulosic polymer is hydroxypropyl methylcellulose.

3. A pramipexole sustained release tablet formulation according to claim 2, wherein: said hydroxypropyl methylcellulose is type 2910 and/or type 2208.

4. A pramipexole sustained release tablet formulation according to claim 1, wherein: said tablet formulation consists of pramipexole or a pharmaceutically acceptable salt thereof, hydroxypropyl methylcellulose, a combination of polyvinylpyrrolidone and vinyl acetate, and magnesium stearate.

5. A pramipexole sustained release tablet formulation according to claim 1, wherein: said tablet formulation comprising pramipexole or a pharmaceutically acceptable salt thereof, also comprising:
 (a) at least one neutral water swelling cellulosic polymer and optionally excipients, the resulting tablet providing a pH-independent in vitro release characteristics in a range of pH 1 to 7.5; and/or
 (b) at least one neutral water swelling noncellulosic polymer and optionally excipients, the resulting tablet providing a pH independent release characteristic in the range of pH 1 to 7.5.

6. A method of manufacturing a sustained release tablet formulation according to claim 1, by a direct compression method comprising the steps of:
 (1) pramipexole or a pharmaceutically acceptable salt thereof with the neutral cellulosic polymer(s) to be pre-mixed to obtain a pre-mixture in a mixer;
 (2) dry screening the pre-mixture through a screen in order to separate cohesive particles to improve uniformity of the contents;
 (3) mixing the pre-mixture of the step (2) in the mixer, and added the remaining excipients to the mixer and the mixing is to be continued;
 (4) the final mixture is tabletted on to a suitable tablet press in order to prepare a matrix tablet.

7. A method of manufacturing a sustained release tablet formulation according to claim 1, by a wet granulation method comprising the steps of:
 (1) pramipexole or a pharmaceutically acceptable salt thereof with the neutral cellulosic polymer(s) to be pre-mixed to obtain a pre-mixture in a mixer;
 (2) dry screening the pre-mixture through a screen in order to separate cohesive particles to improve uniformity of the contents;
 (3) mixing the pre-mixture of the step (2) in the mixer, and add the neutral noncellulosic polymer(s) to the mixer and mixing is to be continued;
 (4) by adding a suitable binder or wetting agent, the mixture of step (3) is made into wet granules;
 (5) drying the granules of step (4) in a fluidized bed dryer or a drying oven;
 (6) mixing the dried granules of step (5) with excipients in the mixer, in order to obtain the final mixture;
 (7) the final mixture of step (6) is tabletted on to a suitable tablet press in order to prepare a matrix tablet.

8. A method of manufacturing a sustained release tablet formulation according to claim 1, by a dry granulation method comprising the steps of:
 (1) pramipexole or a pharmaceutically acceptable salt thereof with the neutral cellulosic polymer(s) to be pre-mixed to obtain a pre-mixture in a mixer;
 (2) dry screening the pre-mixture through a screen in order to separate cohesive particles to improve uniformity of the contents;
 (3) mixing the pre-mixture of the step (2) in the mixer, and adding the noncellulosic neutral polymer(s) to the mixer and mixing is to be continued;
 (4) compacting the mixture of the step (3) on to a suitable roller compactor;
 (5) suitably milling or sieving the ribbon of small particles obtained from step (4);
 (6) mixing the dried granules of step (5) with excipients in the mixer, in order to obtain the final mixture;
 (7) the final mixture of step (6) is tabletted on to a suitable tablet press in order to prepare a matrix tablet.

9. A method for the treatment of Parkinson's disease and complications or symptoms associated therewith, comprising administering the sustained release tablet formulation according to claim 1 to a subject in need thereof.

* * * * *